United States Patent [19]

Yarovesky et al.

[11] Patent Number: 5,529,492

[45] Date of Patent: Jun. 25, 1996

[54] ANTERIOR TOOTH CHARACTERIZATION GUIDE AND METHOD OF SELECTING CHARACTERIZATIONS FOR AN ANTERIOR TOOTH PROSTHESIS

[75] Inventors: Uriel Yarovesky, Woodland Hills; Daniel Materdomini, Topanga Canyon, both of Calif.

[73] Assignee: Dental Illusions, Woodland Hills, Calif.

[21] Appl. No.: 367,742

[22] Filed: Jan. 4, 1995

Related U.S. Application Data

[63] Continuation-in-part of Ser. No. 297,251, Aug. 26, 1994, Pat. No. 5,482,459.

[51] Int. Cl.$^6$ .............................. A61C 19/10; A61C 5/00
[52] U.S. Cl. ................................. 433/26; 433/215
[58] Field of Search ................... 433/26, 203.1, 433/215

[56] References Cited

U.S. PATENT DOCUMENTS

| | | | |
|---|---|---|---|
| 4,207,678 | 6/1980 | Jeannette | 433/203.1 |
| 4,657,399 | 4/1987 | Hall | 433/26 |
| 4,802,850 | 2/1989 | Boon | 433/26 |
| 4,828,117 | 5/1989 | Panzera et al. | 433/203.1 |
| 5,004,417 | 4/1991 | Giaramita | 433/26 |
| 5,114,340 | 5/1992 | Hahn | 433/26 |
| 5,240,414 | 8/1993 | Thompson | 433/26 |

*Primary Examiner*—Cary E. O'Connor
*Attorney, Agent, or Firm*—Kelly, Bauersfeld & Lowry

[57] ABSTRACT

An anterior tooth characterization guide includes several sets of anterior tooth samples which each have differing characteristics. The characterization guide is useful in connection with a method for selecting characterizations for an anterior tooth prosthesis, which permits a dentist to relay to a laboratory an accurate representation of the tooth prosthesis to be manufactured. In this regard, the characterization guide is utilized to select a dentin color for the tooth prosthesis from several tooth samples in which the incisal color is constant. The body to incisal relation for the tooth prosthesis may also be selected from tooth samples in which the dentin is constant, and the amount of white stain for the tooth prosthesis may be selected from the tooth samples in which the dentin and enamel are constant. Similarly, the tooth samples of the characterization guide are utilized to select the incisal color, the dentin structure and translucent effect, and additional characterization features including cracking, spotting and hallow.

29 Claims, 4 Drawing Sheets

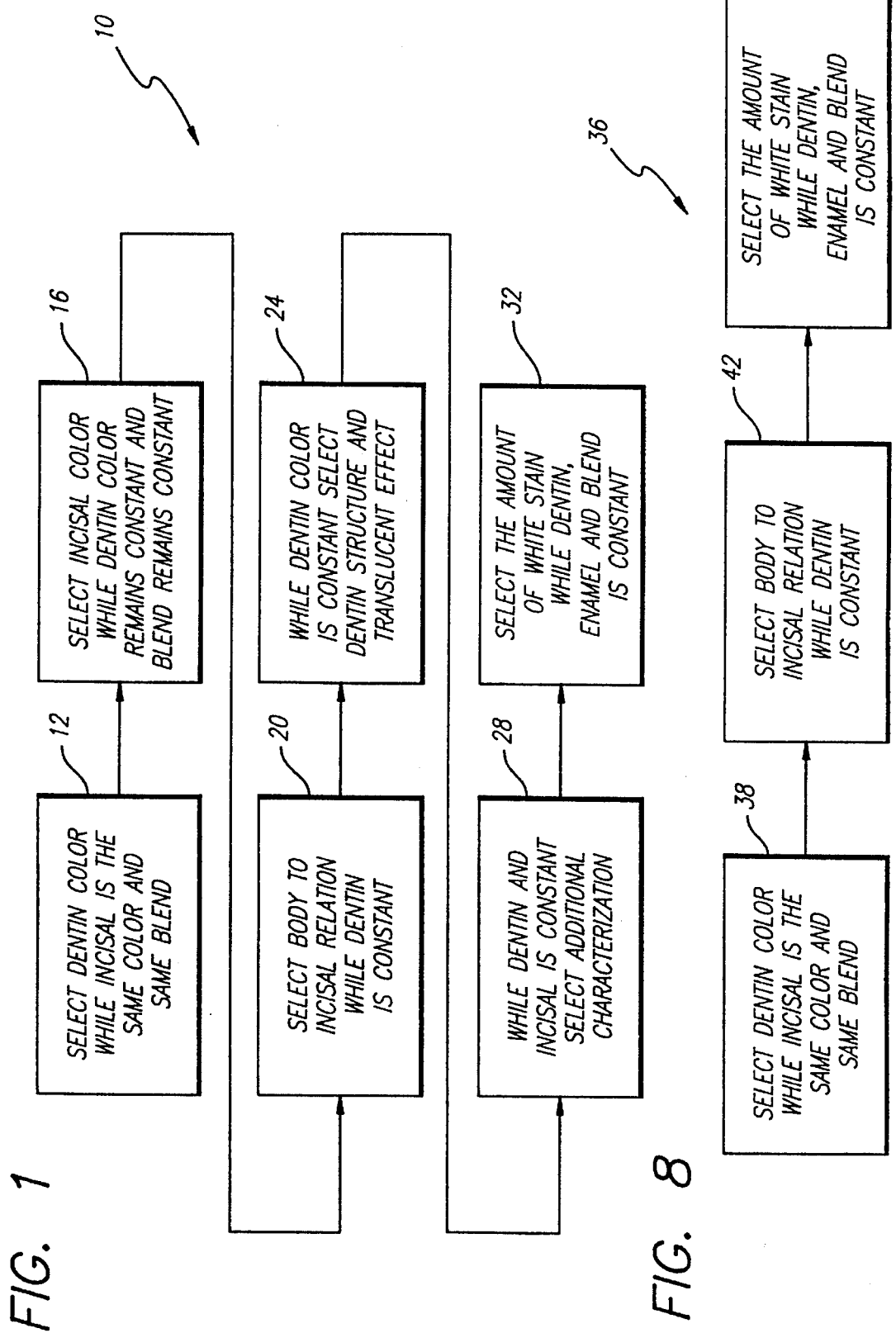

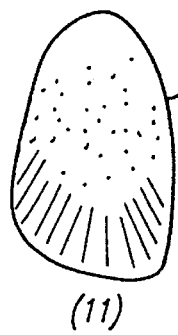 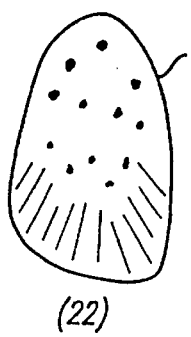 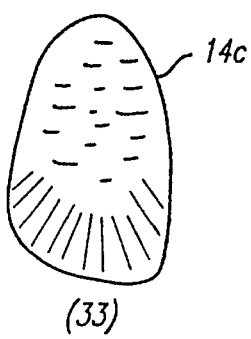 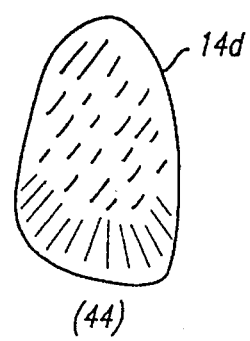
(11)     (22)     (33)     (44)
FIG. 2A    FIG. 2B    FIG. 2C    FIG. 2D
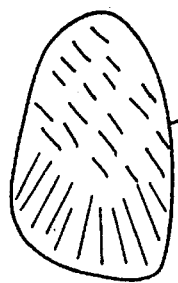 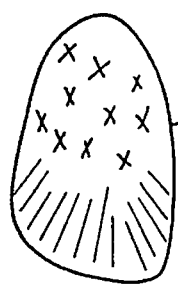 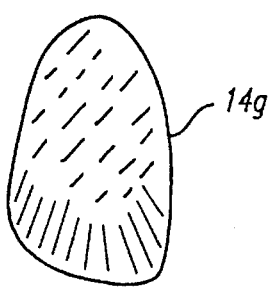
(55)     (66)     (77)
FIG. 2E    FIG. 2F    FIG. 2G
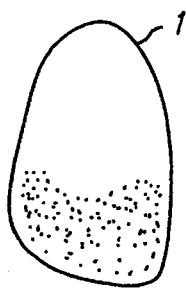 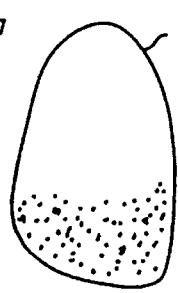 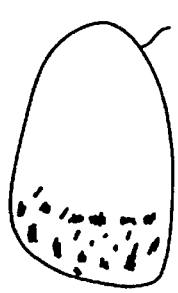 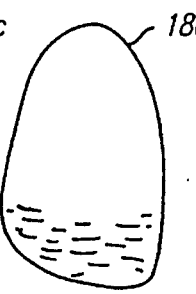 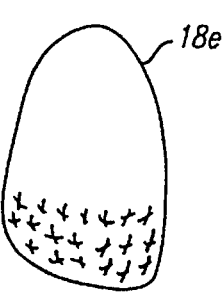
LIGHT    MEDIUM    DARK    GRAY    WHITE GRAY
FIG. 3A   FIG. 3B   FIG. 3C   FIG. 3D   FIG. 3E
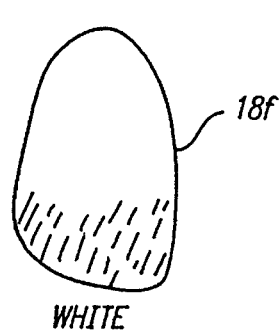 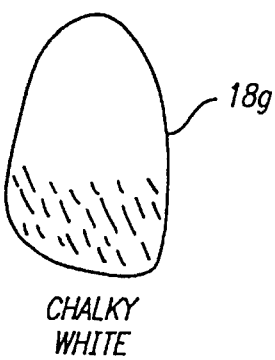
WHITE        CHALKY WHITE
FIG. 3F        FIG. 3G

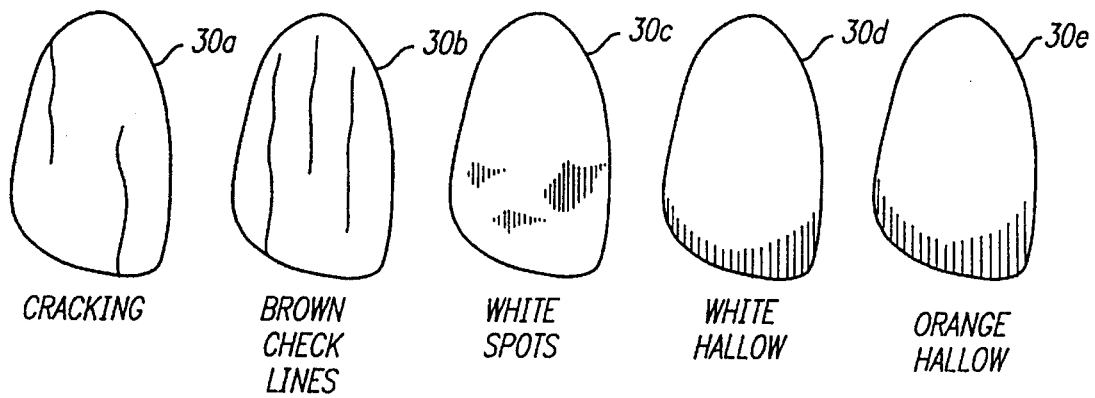
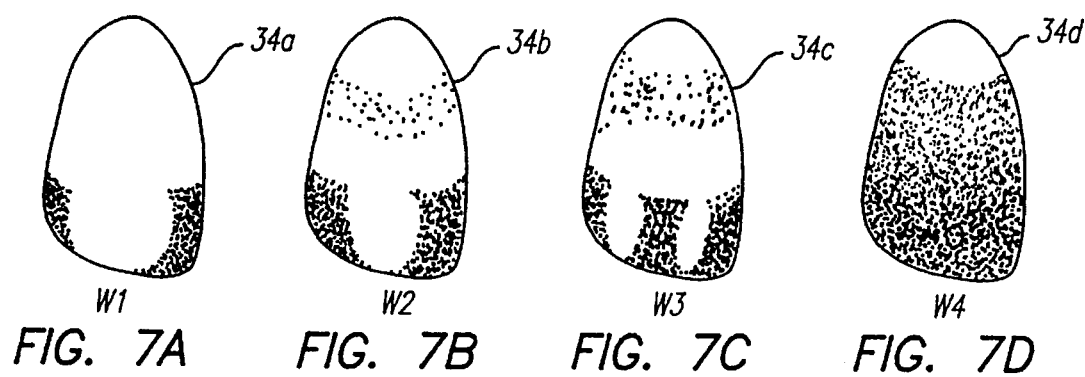
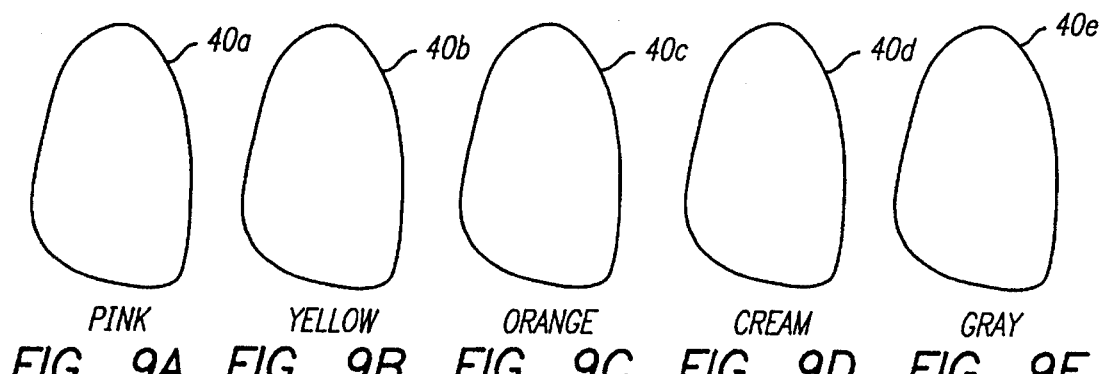
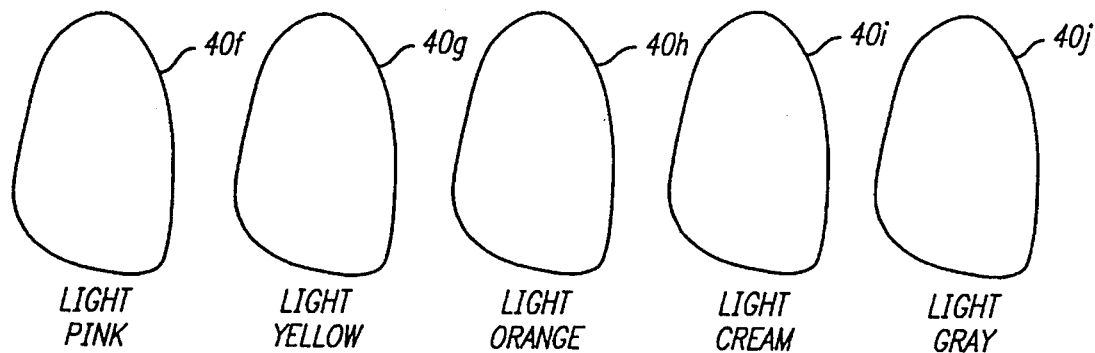

ANTERIOR TOOTH CHARACTERIZATION GUIDE AND METHOD OF SELECTING CHARACTERIZATIONS FOR AN ANTERIOR TOOTH PROSTHESIS

RELATED APPLICATION

This is a continuation-in-part of U.S. Patent application Ser. No. 08/297,251, filed Aug. 26, 1994, now U.S. Pat. No. 5,482,459, and entitled POSTERIOR TOOTH SHADE GUIDE AND METHOD OF SELECTING CHARACTERIZATION FOR A TOOTH PROSTHESIS.

BACKGROUND OF THE INVENTION

This invention relates generally to the field of dentistry. More specifically, the present invention relates to an anterior tooth characterization guide and a method of selecting characterizations for an anterior tooth prosthesis.

Accurate communication between dentists and laboratories that manufacture tooth prostheses has been a subject of continuous concern as technology progresses. When instructing the laboratory to construct a tooth prosthesis, it is desirable to manufacture the prosthesis in such a manner that it is virtually indistinguishable from the surrounding natural teeth.

Many manufacturers of tooth prostheses provide performes samples of multi-color, multi-layer fabricated teeth as references for color. The dentist may communicate to the lab regarding the desired color of the tooth prosthesis utilizing a shade guide having a number of these fabricated teeth for reference. In this regard, the dentist typically holds a sample tooth against the mouth in an attempt to find the closest sample to the natural tooth.

Such dental shade guides typically include a number of anterior tooth-shaped and detailed samples. Although the anterior tooth samples of typical prior dental shade guides usually permit the dentist to match a general color of the tooth prosthesis to be manufactured with the color of a patient's natural teeth, they do not provide suitable means for permitting the dentist to relay to the laboratory the characteristics to be incorporated into the tooth prosthesis to match the natural tooth. In this regard, variables which should be taken into account when manufacturing a tooth prosthesis include the dentin color, the incisal color, the body to incisal relation or "blend", the dentin structure and translucent effect, and the amount of white stain. Additional characterization features may include cracking, brown check lines, white spots and hallow.

Accordingly, there has been a need for an anterior tooth characterization guide and method of selecting characterizations for an anterior tooth prosthesis which can simply, yet effectively, facilitate accurate communication of the desired characteristics of a tooth prosthesis between the dentist and the laboratory. The present invention fulfills these needs and provides other related advantages.

SUMMARY OF THE INVENTION

The present invention resides in a novel anterior tooth characterization guide and a related method, which permit a dentist to relay to the laboratory an accurate representation of a tooth prosthesis to be manufactured. The anterior tooth characterization guide includes a plurality of anterior tooth samples bearing different tooth characteristics. From these tooth samples the dentist is able to choose a suitable dentin color, an incisal color, and a body to incisal relation or "blend" for the tooth prosthesis. If desired, additional anterior tooth characteristics may also be selected, including a dentin structure and translucent effect for the tooth prosthesis, the amount of white stain, and additional characterizations including cracking, check lines, spotting, white hallow and orange hallow.

With the anterior tooth characterization guide a dentist and the laboratory may utilize a method for selecting characterizations of a tooth prosthesis wherein the anterior tooth samples are referred to in specifying the precise characteristics to be embodied in the tooth prosthesis. In a preferred form of the invention, the method for selecting characterizations for an anterior tooth prosthesis comprises the step of selecting a dentin color for the tooth prosthesis from a portion of a set of tooth samples in which the incisal color is constant. Next, an incisal color is selected for the tooth prosthesis from a portion of the set of tooth samples in which the dentin color is constant. A body to incisal relation or blend for the tooth prosthesis is then selected from a portion of the set of tooth samples in which the dentin is constant.

More specifically, the method for selecting characterizations for an anterior tooth prosthesis includes the steps of selecting a dentin color for the tooth prosthesis from a first set of tooth samples in which incisal color and blend is constant. An incisal color is then selected for the tooth prosthesis from a second set of tooth samples in which the dentin color and blend is constant. The body to incisal relation for the tooth prosthesis is selected from a third set of tooth samples in which the dentin is constant. Next, a dentin structure and translucent effect for the tooth prosthesis is selected from a fourth set of tooth samples in which the dentin color is constant. Additional characterizations for the tooth prosthesis such as cracking, spotting and hallow are selected from a fifth set of tool samples in which the dentin and incisal are constant. Finally, the amount of white stain for the tooth prosthesis is selected from a sixth set of tooth samples in which the dentin and enamel and blend are constant.

The method of the present invention may be advantageously utilized to select characterizations for an anterior tooth prosthesis to match bleach white teeth. In this case, the dentin color for the tooth prosthesis is selected from a portion of a set of tooth samples in which the incisal color is constant, and wherein the tooth samples have pink, yellow, orange, green or grey dentin within a white incisal overlay. All that is then required to complete the characterization selection process is to select a body to incisal relation for the tooth prosthesis from a set of tooth samples in which the dentin is constant, and select the amount of white stain for the tooth prosthesis from a set of tooth samples in which the dentin and enamel are constant.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a flow chart illustrating the steps of the method of selecting characterizations for an anterior tooth prosthesis in accordance with the present invention;

FIGS. 2A–2G are front elevational views of a set of anterior tooth samples, wherein the incisal of each tooth sample has the same color and same blend, but the dentin color varies among the tooth samples of the set;

FIGS. 3A–3G are front elevational views of a set of anterior tooth samples wherein the dentin color and blend remains constant, but the incisal color varies among the tooth samples of the set;

FIGS. 6A–6E are front elevational views of a set of anterior tooth samples wherein the dentin and incisal are constant, but the samples vary in that they show additional characterization features such as cracking, brown check lines, white spots, white hallow and orange hallow;

FIGS. 7A–7D are front elevational views of a set of anterior tooth samples wherein the dentin, enamel and blend is constant, but the amount of white stain varies among the samples;

FIG. 8 is a flow chart illustrating the steps of a simplified method of selecting characterizations for a tooth prosthesis for bleach white teeth in accordance with the present invention; and FIGS. 9A–9J are front elevational views of bleach white anterior tooth samples utilized in connection with the method of FIG. 8, wherein the incisal is the same color and same blend, and the dentin color varies among the samples.

DETAILED DESCRIPTION OF THE PREFERRED EMBODIMENTS

Figures 4A, 4B, 4C, 4D, 4E:
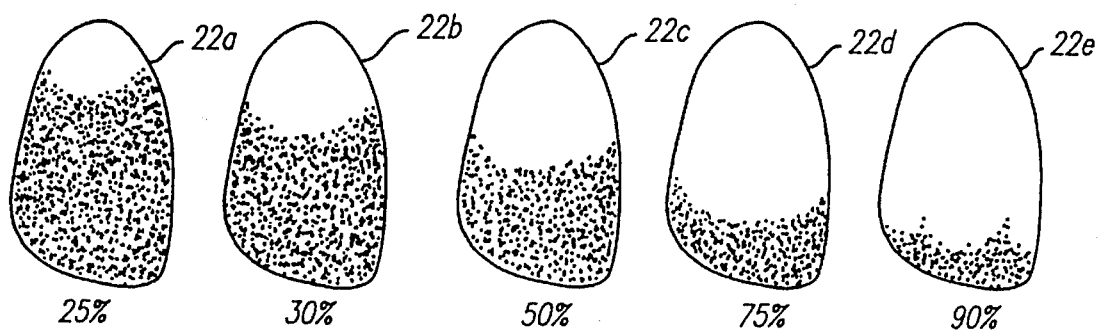
FIGS. 4A–4E are front elevational views of a set of anterior tooth samples wherein the dentin is constant among the samples, but the body to incisal relation (the blend) varies.

As shown in the drawings for purposes of illustration, the present invention is concerned with a method of selecting characterizations for an anterior tooth prosthesis, which method is generally designated in FIG. 1 by the reference number 10. The improved method 10 is practiced in connection with an anterior tooth characterization guide which comprises a plurality of anterior tooth samples as shown in FIGS. 2–7 and 9, which will be discussed in detail below. The anterior tooth characterization guide and the method 10 of selecting characterizations for a tooth prosthesis, permit a dentist to relay to the laboratory an accurate representation of a tooth prosthesis to be manufactured.

In accordance with the present invention, the method 10 for selecting characterizations for an anterior tooth prosthesis begins with the step of selecting a dentin color for the tooth prosthesis, as indicated by the block 12 of FIG. 1. With reference to FIGS. 2A–2G, several anterior tooth samples 14a–14g are provided for this purpose. The incisal color and blend of the tooth samples 14a–14g is constant to permit a true comparison of the dentin color and appropriate selection by the dentist. The dentin colors may include pink, light pink, yellow, light yellow, orange, light orange, cream, light cream, grey and light grey, and the tooth samples will bear a simple numerical indicia nomenclature to identify each, for example (11)–(77). The dentist would select the tooth sample 14a–14g having he desired dentin color to be utilized with the tooth prosthesis and record the information for transmission to the laboratory.

The next step of the method 10, indicated by block 16 of FIG. 1, is to select an incisal color for the tooth prosthesis. In this regard a second set of tooth samples 18a–18g is provided in which the dentin color and blend is constant. FIG. 3A illustrates a tooth sample 18a having a light incisal color; FIG. 3B illustrates a tooth sample 18b having a medium incisal color; FIG. 3C illustrates a tooth sample 18c having a dark incisal color; FIG. 3 D illustrates a tooth sample 18d having a grey incisal color; FIG. 3E illustrates a tooth sample 18e having a white grey incisal color; FIG. 3F illustrates a tooth sample 18f having a white incisal color; and FIG. 3 G illustrates a tooth sample 18g having a chalky white incisal color. The dentist would select the desired incisal color to be applied to the tooth prosthesis from the tooth samples 18a–18g, and record the selection utilizing a short hand notation such as light, medium, dark, grey, white grey, white or chalky white.

Next, as illustrated in block 20 of FIG. 1, the body to incisal relation (blend) for the tooth prosthesis is selected. FIGS. 4A–4E show a third set of tooth samples 221–22E in which the dentin is constant and which have varying body to incisal relations. FIG. 4A shows a tooth sample 22a wherein the body to incisal relation is 25% body and 75% incisal as the dominant characteristics. FIG. 4 B illustrates a tooth sample 22b wherein the body to incisal relation is 30% body and 70% incisal as the dominant characteristics. FIG. 4C shows a tooth sample 22c wherein the body to incisal relation is 50% body and 50% incisal as the dominant characteristics. FIG. 4D shows a tooth sample 22d wherein the body to incisal relation is 75% body and 25% incisal as the dominant characteristics. FIG. 4E shows a tooth sample 22e wherein the body to incisal relation is 90% body and 10% incisal as the dominant characteristics. As in all of the cases noted above, the dentist selects from among these tooth samples 22a–22e to determine which most accurately reflects the characterization to be included in the tooth prosthesis to be manufactured.

As indicated by block 24 in FIG. 1, the next step is to select a dentin structure and translucent effect for the tooth prosthesis. Reference is made to a fourth set of tooth samples 26a–26k (FIGS. 5A–5K) in order to select the desired structure and effect. In the fourth set of tooth samples 26a–26k, the dentin color is constant so that the only variable is the dentin structure and translucent effect. The dentist simply selects which of the tooth samples 26a–26k most accurately shows the dentin structure and translucent effect desired for the tooth prosthesis to match natural tooth, and records the information utilizing any type of notation that will be understood by the laboratory, for example 5A–5K.

Next, as illustrated in block 28 of FIG. 1, additional characterizations for the tooth prosthesis are selected. In this regard, reference is made to a fifth set of tooth samples 30a–30e (FIGS. 6A–6E) in which the dentin and incisal are constant. FIG. 6A illustrates a tooth sample 30a having cracking as a characteristic; FIG. 6B illustrates a tooth sample 30b having brown check lines as a characteristic; FIG. 6C illustrates a tooth sample 30c having white spots as an additional characteristic; FIG. 6D shows a tooth sample 30d having white hallow as an additional tooth characteristic; and FIG. 6E illustrates a tooth sample 30e having orange hallow as an additional tooth characteristic. When recording the selected additional characteristic desired for the tooth prosthesis, if any, the dentist may simply utilize the notations cracking, brown check lines, white spots, white hallow or orange hallow. Of course, additional tooth samples may be provided which show other characterizations for the tooth prosthesis.

As a final step in the method 10, as illustrated in block 32 of FIG. 1, the amount of white stain for the tooth prosthesis is selected. With reference to FIGS. 7A–7D, a sixth set of tooth samples 34a–34d are provided which have differing white stain characteristics, wherein the dentin and enamel and blend are constant. FIG. 7A shows a tooth sample 34a having a light white stain; FIG. 7B shows a tooth sample 34b having a medium white stain; FIG. 7C shows a tooth sample 34c having a heavy white stain; and FIG. 7D shows a tooth sample 34d having a very heavy white stain. The white stain shown on the samples 34a–34d is indicated through simple nomenclature such as W1–W4. The dentist simply selects which of the tooth samples 34a–34d most accurately shows the white stain characteristic desired for the tooth prosthesis to be manufactured.

Figures 5A, 5B, 5C, 5D:
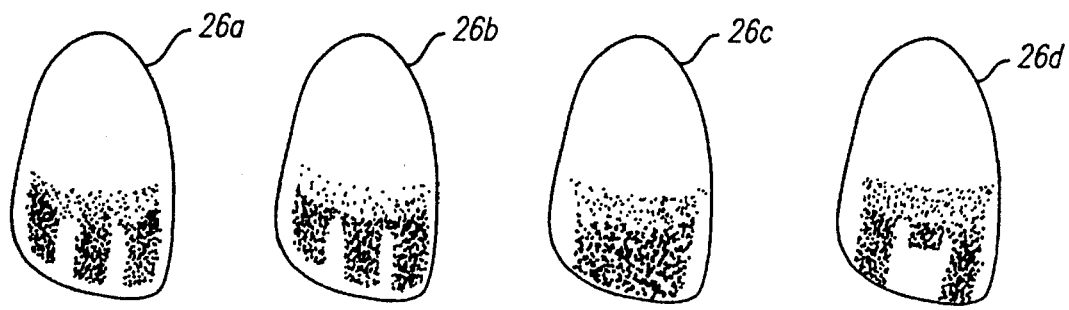
FIGS. 5A–5K are front elevational views of a set of anterior tooth samples wherein the dentin color is constant but the dentin structure and translucent effect varies among the samples.
Figures 5E, 5F:
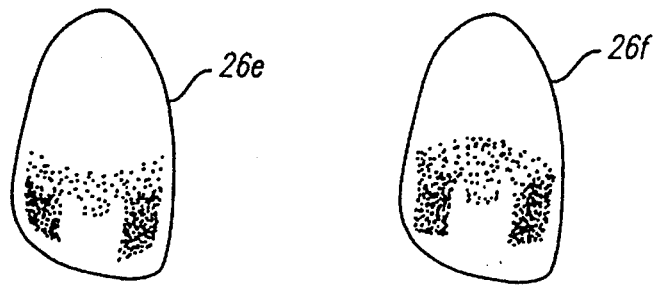
Figures 5G, 5H, 5I, 5J, 5K:
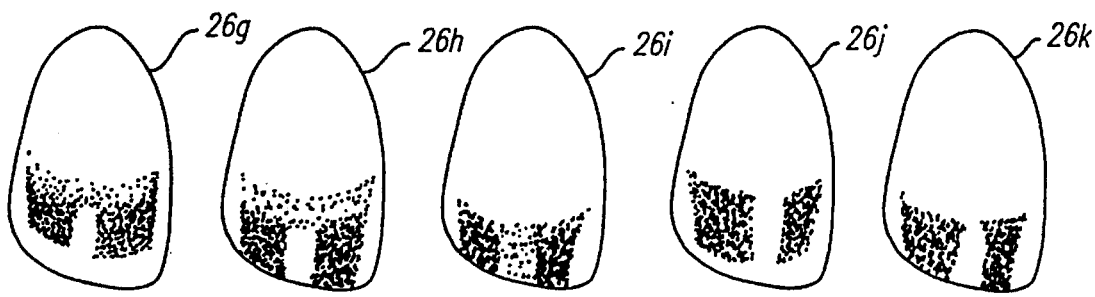

From the foregoing it is to be appreciated that the anterior tooth characterization guide of the present invention may be advantageously utilized by dentists and laboratory technicians alike to ensure more accurate communication regarding the characteristics of a tooth prosthesis to be manufactured. By way of example, a dentist may submit to a laboratory a request to manufacture an anterior tooth prosthesis with the designation "(22), medium, 24%, 5I, white hallow, W1". The laboratory technician would then know, from the foregoing, that the dentin color for the tooth prosthesis would correspond to the tooth sample 14b shown in FIG. 2B, the incisal color for the tooth prosthesis would match the color of the tooth sample 18b shown in FIG. 3B, the body to incisal relation would be 25% as shown in the tooth sample 22a of FIG. 4A, the dentin structure and translucent effect would be as shown in the tooth sample 26i as shown in FIG. 5I, that the additional characterization would be a white hallow as shown in the tooth sample 30d of FIG. 6D, and that the amount of white stain would correspond to the tooth sample 34a as shown in FIG. 7A. Of course, additional information may be transmitted to the laboratory from the dentist, including a drawing of additional characterizations to be included in the tooth prosthesis.

FIG. 8 illustrates another method 36 for selecting characterizations for a tooth prosthesis which, although related to the method 10 shown in FIG. 1, is simplified for use with bleach white teeth. In this alternative method 36 utilized with bleach white teeth, the first step, as shown in block 38 of FIG. 8, is to select a dentin color for the tooth prosthesis from a first set of tooth samples 40a–40j (FIGS. 9A–9J) in which the incisal color and blend is constant. A separate set of tooth samples 40a–40j is utilized in this regard (in comparison with the tooth samples 14a–14g), since it is desired that the incisal color and blend be bleached. FIG. 9A illustrates a tooth sample 40a wherein the dentin color is pink; FIG. 9B illustrates a tooth sample 40b wherein the dentin color is yellow; FIG. 9C illustrates a tooth sample 40c wherein the dentin color is orange; FIG. 9D illustrates a tooth sample 40d wherein the dentin color is cream; FIG. 9E illustrates a tooth sample 40e wherein the dentin color is grey; FIG. 9F illustrates a tooth sample 40f wherein the dentin color is light pink; FIG. 9G illustrates a tooth sample 40g wherein the dentin color is light yellow; FIG. 9H illustrates a tooth sample 40h wherein the dentin color is light orange; FIG. 9I illustrates a tooth sample 40i wherein the dentin color is light cream; and FIG. 9J illustrates a tooth sample 40j wherein the dentin color is a light grey. The dentist selects the dentin color to be applied to the tooth prosthesis from the tooth samples 40a–40j and records the same utilizing any accepted shorthand notation, such as the aforementioned colors.

Next, as illustrated in block 42 of FIG. 8, the body to incisal relation (blend) for the tooth prosthesis is selected in the same manner as discussed above in connection with the tooth samples 22a–22e and FIGS. 4A–4E. Then, as a final step in the method 36, as illustrated by block 44 of FIG. 8 the amount of white stain is selected for the tooth prosthesis. In this regard, the discussion above relating to the tooth samples 34a–34d and FIGS. 7A–7D apply equally to the method 36 of FIG. 8 to the method 10 of FIG. 1.

Although two particular embodiments of the invention have been described in detail for purposes of illustration, various modifications may be made without departing from the spirit and scope of the invention. For example, it will be understood that while the anterior tooth characterization guide utilizes actual tooth samples for purposes of the comparisons and selections of the desired tooth prosthesis characteristics, the methods of the present invention may be practiced utilizing prints and disposable plastic representations of the anterior tooth characterization guide. Accordingly, the invention is not to be limited, except as by the appended claims.

We claim:

1. A method for selecting characterizations for an anterior tooth prosthesis, comprising the steps of:

selecting a dentin color for the tooth prosthesis from a portion of a set of tooth samples, in which portion the incisal color is constant;

selecting a body to incisal relation for the tooth prosthesis from a portion of the set of tooth samples, in which portion the dentin is constant; and selecting the amount of white stain for the tooth prosthesis from a portion of the set of tooth samples, in which portion the dentin and enamel are constant.

2. The method of claim 1, wherein during the step of selecting a dentin color for the tooth prosthesis, the body to incisal relation is constant among the portion of the tooth samples utilized.

3. The method of claim 1, wherein during the step of selecting the amount of white stain for the tooth prosthesis, the body to incisal relation is constant for the portion of the tooth samples utilized.

4. The method of claim 1, including the step of selecting an incisal color for the tooth prosthesis from a portion of the set of tooth samples, in which portion the dentin color is constant.

5. The method of claim 4, wherein during the step of selecting an incisal color for the tooth prosthesis, the body to incisal relation is constant for the portion of the tooth samples utilized.

6. The method of claim 1, including the step of selecting a dentin structure and translucent effect for the tooth prosthesis from a portion of the set of tooth samples, in which portion the dentin color is constant.

7. The method of claim 1, including the step of selecting additional characterizations for the tooth prosthesis from a portion of the set of tooth samples, in which portion the dentin and incisal are constant.

8. The method of claim 7, wherein the step of selecting additional characterizations for the tooth prosthesis includes the step of selecting from tooth samples bearing characteristics including cracking, spotting and hallow.

9. The method of claim 1, wherein the step of selecting a dentin color for the tooth prosthesis includes the step of selecting from tooth samples having pink, yellow, orange, cream or grey dentin within a white incisal overlay.

10. A method for selecting characterizations for an anterior tooth prosthesis, comprising the steps of:

selecting a dentin color for the tooth prosthesis from a portion of a set of tooth samples, in which portion the incisal color is constant;

selecting an incisal color for the tooth prosthesis from a portion of the set of tooth samples, in which portion the dentin color is constant; and selecting a body to incisal relation for the tooth prosthesis from a portion of the set of tooth samples, in which the dentin in constant.

11. The method of claim 10, including the step of selecting a dentin structure and translucent effect for the tooth prosthesis from a portion of the set of tooth samples, in which portion the dentin color is constant.

12. The method of claim 10, including the step of selecting additional characterizations for the tooth prosthesis from a portion of the set of tooth samples, in which portion the dentin and incisal are constant.

13. The method of claim 12, wherein the step of selecting additional characterizations for the tooth prosthesis includes the step of selecting from tooth samples bearing characteristics including cracking, spotting and hallow.

14. The method of claim 10, including the step of selecting the amount of white stain for the tooth prosthesis from a portion of the set of tooth samples, in which portion the dentin and enamel are constant.

15. The method of claim 14, wherein during the step of selecting the amount of white stain for the tooth prosthesis, the body to incisal relation is constant for the portion of the tooth samples utilized.

16. The method of claim 10, wherein the step of selecting a dentin color for the tooth prosthesis includes the step of selecting from tooth samples having pink, yellow, orange, cream or grey dentin within a white incisal overlay.

17. The method of claim 10, wherein during the step of selecting a dentin color for the tooth prosthesis, the body to incisal relation is constant among the portion of the tooth samples utilized.

18. The method of claim 10, wherein during the step of selecting an incisal color for the tooth prosthesis, the body to incisal relation is constant for the portion of the tooth samples utilized.

19. A method for selecting characterizations for an anterior tooth prosthesis, comprising the steps of:

selecting a dentin color for the tooth prosthesis from a first set of tooth samples in which the incisal color and a body to incisal relation is constant;

selecting an incisal color for the tooth prosthesis from a second set of the tooth samples in which the dentin color and the body to incisal relation is constant;

selecting a body to incisal relation for the tooth prosthesis from a third set of tooth samples in which the dentin is constant;

selecting a dentin structure and translucent effect for the tooth prosthesis from a fourth set of tooth samples in which the dentin color is constant; and selecting the amount of white stain for the tooth prosthesis from a fifth set of tooth samples in which the dentin and enamel and the body to incisal relation are constant.

20. The method of claim 19, including the step of selecting additional characterizations for the tooth prosthesis from a sixth set of tooth samples in which the dentin and incisal are constant, wherein the tooth samples have characteristics including cracking, spotting and hallow.

21. An anterior tooth characterization guide for selecting characterizations for a tooth prosthesis, comprising:

a first set of tooth samples in which incisal color is constant, for providing means for selecting a dentin color for the tooth prosthesis;

a second set of tooth samples in which the dentin is constant, for providing means for selecting a body to incisal relation for the tooth prosthesis; and a third set of tooth samples in which the dentin and enamel are constant, for providing means for selecting the amount of white stain for the tooth prosthesis.

22. The anterior tooth characterization guide of claim 21, wherein the body to incisal relation color of the first set of tooth samples is constant.

23. The anterior tooth characterization guide of claim 21, wherein the body to incisal relation of the third set of tooth samples is constant.

24. The anterior tooth characterization guide of claim 21, including a fourth set of tooth samples in which the dentin color is constant, for providing means for selecting an incisal color for the tooth prosthesis.

25. The anterior tooth characterization guide of claim 24, wherein the body to incisal relation of the fourth set of tooth samples is constant.

26. The anterior tooth characterization guide of claim 21, including a fifth set of tooth samples in which the dentin color is constant, for providing means for selecting a dentin structure and translucent effect for the tooth prosthesis.

27. The anterior tooth characterization guide of claim 21, including a sixth set of tooth samples in which the dentin and incisal are constant, for providing means for selecting additional characterizations for the tooth prosthesis.

28. The anterior tooth characterization guide of claim 27, wherein the sixth set of tooth samples includes examples of cracking, spotting and hallow.

29. The anterior tooth characterization guide of claim 21, wherein the third set of tooth samples includes tooth samples having pink, yellow, orange, cream and grey dentin within a white incisal overlay.

* * * * *